(12) United States Patent
Ikeya et al.

(10) Patent No.: US 6,833,381 B2
(45) Date of Patent: Dec. 21, 2004

(54) TNF-α INHIBITORS

(75) Inventors: Kazuaki Ikeya, Ikoma-gun (JP); Takahito Kitayoshi, Suita (JP)

(73) Assignee: Takeda Chemical Industries, Ltd., Osaka (JP)

(*) Notice: Subject to any disclaimer, the term of this patent is extended or adjusted under 35 U.S.C. 154(b) by 114 days.

(21) Appl. No.: 10/203,805

(22) PCT Filed: Feb. 15, 2001

(86) PCT No.: PCT/JP01/01069

§ 371 (c)(1),
(2), (4) Date: Aug. 14, 2002

(87) PCT Pub. No.: WO01/60362

PCT Pub. Date: Aug. 23, 2001

(65) Prior Publication Data

US 2003/0055039 A1 Mar. 20, 2003

(30) Foreign Application Priority Data

Feb. 18, 2000 (JP) ........................................ 2000-046828

(51) Int. Cl.$^7$ .................. A61K 31/4164; C07D 257/04; C07D 403/04
(52) U.S. Cl. .................... 514/397; 548/251; 548/306.1; 514/399
(58) Field of Search .............................. 548/251, 306.1, 548/309.7, 310.1; 514/397, 399, 394

(56) References Cited

U.S. PATENT DOCUMENTS 5,721,263 A * 2/1998 Inada et al. .................. 514/381
6,228,874 B1 * 5/2001 Inada et al. .................. 514/364

FOREIGN PATENT DOCUMENTS

| EP | 0 459 136 | 12/1991 |
|---|---|---|
| EP | 0 612 523 | 8/1994 |
| EP | 0 612 524 | 8/1994 |
| EP | 0 622 077 | 11/1994 |
| JP | 2000-159671 | 6/2000 |
| WO | 95/06410 | 3/1995 |
| WO | 95/21609 | 8/1995 |
| WO | 96/36336 | 11/1996 |
| WO | 97/37688 | 10/1997 |

OTHER PUBLICATIONS

A. Hahn et al., "Activation of Human Peripheral Monocytes by Angiotensin II", FEBS Letters, vol. 347, pp. 178–180, 1994.

T. Tsutamoto et al., "Angiotensin II Type I Receptor Antagonist Decreases Plasma Levels of Tumor Necrosis Factor Alpha, Interleukin–6 and Soluble Adhesion Molecules in Patients with Chronic Heart Failure", Journal of the American College of Cardiology, vol. 35, No. 3, pp. 714–721, Mar. 1, 2000.

A. Peeters et al., "The effect of Resin–Angiotensin System Inhibitors on Pro– and anti–inflammatory Cytokine Production", Immunology, vol. 94, pp. 376–379, 1998.

* cited by examiner

*Primary Examiner*—Joseph K. McKane
*Assistant Examiner*—Golam M M Shameem
(74) *Attorney, Agent, or Firm*—Wenderoth, Lind & Ponack, L.L.P.

(57) ABSTRACT

TNF-α inhibitors containing a heterocyclic compound having angiotensin II antagonistic activity which are useful as preventives/remedies for inflammatory diseases, etc.

11 Claims, No Drawings

TNF-α INHIBITORS

This application is a 371 of PCT/JP01/01069 filed Feb. 15, 2001.

FIELD OF THE INVENTION

The present invention relates to a TNF-α inhibitor which contains a heterocyclic compound having an angiotensin II antagonistic activity, its prodrug or a salt thereof and which is useful as preventives or remedies for an inflammatory disease and the like.

BACKGROUND ART

A TNF (tumor necrosis factor)-α is believed to play an important role in various diseases. For example, chronic rheumatoid arthritis that is an inflammatory disease involves an increased TNF-α production which may lead to the destruction of an articular tissue.

A TNF-α inhibitor which has sufficiently excellent pharmaceutical characteristics such as an excellent prophylactic or therapeutic effect for an inflammatory disease and no side effects, is desired to be developed.

DISCLOSURE OF THE INVENTION

In view of these circumstances described above, the present inventors made an effort to develop an agent useful in inhibiting a TNF-α, and found eventually that a heterocyclic compound having an angiotensin II antagonistic activity, especially a compound having an angiotensin II(AII) antagonistic activity which is represented by a certain structural formula, is extremely effective in inhibiting a TNF-α, and a further investigations were made on the basis of this knowledge and the present invention was completed.

That is, the present invention relates to:

(1) A TNF-α inhibitor comprising a heterocyclic compound having an angiotensin II antagonistic activity (a heterocyclic compound having an angiotensin II receptor-antagonistic action) which is represented by the formula:

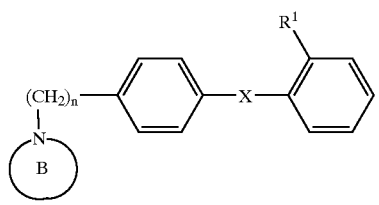

wherein ring B is an optionally substituted nitrogen-containing heterocyclic ring, $R^1$ is a group capable of forming an anion or a group capable of being converted into such a group, X denotes that a phenylene group and a phenyl group are bound directly or through a spacer having 2 or less of atomic chains, and n is an integer of 1 or 2 (except for the compound represented by the formula:

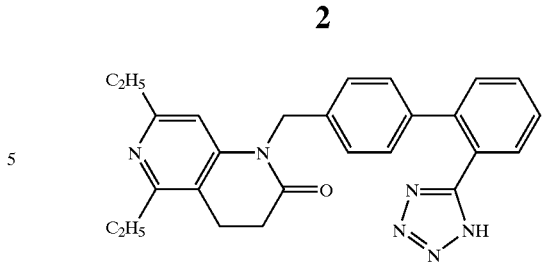

[5,7-dimethyl-1-{[2'-(1H-tetrazol-5-yl)-1,1'-biphenyl-4-yl]methyl}-3,4-dihydro-1,6-naphthylidine-2(1H)-one]), its prodrug or a salt thereof;

(2) An agent according to the above-mentioned (1), wherein the heterocyclic compound is a compound having an oxygen atom in its molecule;

(3) An agent according to the above-mentioned (1), wherein the heterocyclic compound is a compound having an ether bond or a carbonyl group;

(4) An agent according to the above-mentioned (1), wherein ring B is an optionally substituted nitrogen-containing aromatic heterocyclic ring;

(5) An agent according to the above-mentioned (1), wherein ring B is an optionally substituted 5- to 6-membered nitrogen-containing heterocyclic ring;

(6) An agent according to the above-mentioned (1), wherein ring B is an optionally substituted imidazole ring;

(7) An agent according to the above-mentioned (1), wherein the heterocyclic compound is a compound represented by the formula (I):

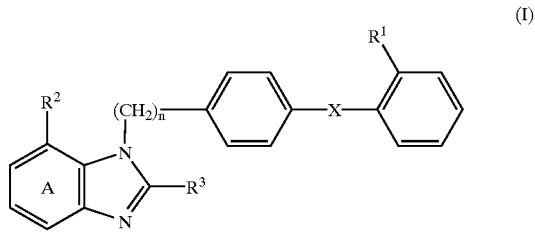

wherein $R^1$ is a group capable of forming an anion or a group capable of being converted into such a group, X denotes that a phenylene group and a phenyl group are bound directly or through a spacer having 2 or less of atomic chains, n is an integer of 1 or 2, ring A is a further optionally substituted benzene ring, $R^2$ is a group capable of forming an anion or a group capable of being converted into such a group, $R^3$ is an optionally substituted hydrocarbon residue which may be bound through a heteroatom;

(8) An agent according to the above-mentioned (1), wherein the heterocyclic compound is losartan, eprosartan, candesartan cilexetil, candesartan, telmisartan, irbesartan, olmesartan or tasosartan;

(9) An agent according to the above-mentioned (1), wherein the heterocyclic compound is 2-ethoxy-1-[[2'-(1H-tetrazol-5-yl)biphenyl-4-yl]methyl]benzimidazole-7-carboxylic acid;

(10) An agent according to the above-mentioned (1), wherein the heterocyclic compound is 1-(cyclohexyloxycarbonyloxy)ethyl-2-ethoxy-1-[[2'-(1H-tetrazol-5-yl)biphenyl-4-yl]methyl]benzimidazole-7-carboxylate;

(11) An agent according to the above-mentioned (1), wherein the heterocyclic compound is 2-ethoxy-1-[[2'-(2,5-dihydro-5-oxo-1,2,4-oxadiazol-3-yl)biphenyl-4-yl]methyl]benzimidazole-7-carboxylic acid;

(12) An agent according to the above-mentioned (1), which is a prophylactic and therapeutic agent for a disease involving a TNF-α (e.g., a disease which is developed or exacerbated as a result of the presence of a TNF-α);

(13) An agent according to the above-mentioned (1), which is an anti-inflammatory agent;

(14) Use of a heterocyclic compound having an angiotensin II antagonistic activity, its prodrug or a salt thereof for inhibiting a TNF-α;

(15) Use of a heterocyclic compound having an angiotensin II antagonistic activity, its prodrug or a salt thereof for the manufacture of a medicament for inhibiting a TNF-α;

(16) A method for inhibiting a TNF-α in mammals comprising administering to a mammal an effective dose of a heterocyclic compound having an angiotensin II antagonistic activity which is represented by the formula:

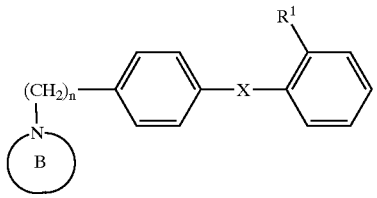

wherein ring B is an optionally substituted nitrogen-containing heterocyclic group, $R^1$ is a group capable of forming an anion or a group capable of being converted into such a group, X denotes that a phenylene group and a phenyl group are bound directly or through a spacer having 2 or less of atomic chains, and n is an integer of 1 or 2 (except for 5,7-dimethyl-1-{[2'-(1H-tetrazol-5-yl)-1,1'-biphenyl-4-yl]methyl}-3,4-dihydro-1,6-naphthylidine-2(1H)-one), its prodrug or a salt thereof;

(17) Use of a heterocyclic compound having an angiotensin II antagonistic activity which is represented by the formula:

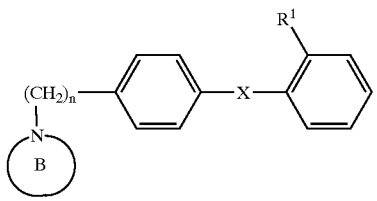

wherein ring B is an optionally substituted nitrogen-containing heterocyclic group, $R^1$ is a group capable of forming an anion or a group capable of being converted into such a group, X denotes that a phenylene group and a phenyl group are bound directly or through a spacer having 2 or less of atomic chains, and n is an integer of 1 or 2 (except for 5,7-dimethyl-1-{[2'-(1H-tetrazol-5-yl)-1,1'-biphenyl-4-yl]methyl}-3,4-dihydro-1,6-naphthylidine-2(1H)-one), its prodrug or a salt thereof for the manufacture of a TNF-α inhibitor; and the like.

A heterocyclic compound having an angiotensin II antagonistic activity according to the present invention, its prodrug or a salt thereof, can be employed advantageously for inhibiting a TNF-α (e.g., inhibiting a TNF-α by inhibiting the production of a TNF-α or by inhibiting a TNF-α receptor).

An angiotensin II-antagonistic activity according to the present invention means a competitive or non-competitive inhibitory effect on the binding of angiotensin II to an angiotensin II receptor on a cell membrane which lead to a reduction in a potent vasoconstrictive effect or vascular smooth muscle-proliferating effect induced by angiotensin.

A heterocyclic compound having an angiotensin II antagonistic activity used in this invention is preferably a non-peptide heterocyclic compound having an antagonistic activity exhibiting an advantageously prolonged duration of action. Such a heterocyclic compound having an angiotensin II antagonistic activity is preferably a compound having an oxygen atom in its molecule, above all, preferably a compound having an ether bond or a carbonyl group (said carbonyl group may be conjugated to form a hydroxyl group), more preferably a compound having ether bond or a ketone derivative, and most preferably an ether derivative.

In the formula above, an "optionally substituted nitrogen-containing heterocyclic ring" represented by ring B is preferably an optionally substituted nitrogen-containing aromatic heterocyclic ring. Such an "optionally substituted nitrogen-containing heterocyclic ring" represented by ring B is preferably an optionally substituted 5- to 6-membered nitrogen-containing heterocyclic ring, especially an optionally substituted 5- to 6-membered nitrogen-containing aromatic heterocyclic ring (e.g., a ring which may be fused to an optionally substituted aromatic ring such as a benzene ring (which may have a substituent group similar to that exemplified as a substituent group on ring A described below), an optionally substituted imidazole ring; typically, an optionally substituted imidazole ring, an optionally substituted benzimidazole ring). A substituent group which may be possessed by a "nitrogen-containing heterocyclic ring" in an "optionally substituted nitrogen-containing heterocyclic ring" represented by ring B may for example be a substituent group similar to that exemplified as a substituent group on ring A described below.

While a non-peptide heterocyclic compound having an angiotensin II antagonistic activity is not limited particularly, those which may be exemplified are imidazole derivatives disclosed in JP-A-56-71073, JP-A-56-71074, JP-A-57-98270, JP-A-58-157768, U.S. Pat. Nos. 4,355,040 and 4,340,598 and the like, modified imidazole derivatives disclosed in EP-253310, EP-291969, EP-324377, EP-403158, WO-9100277, JP-A-63-23868 and JP-A-1-117876 and the like, pyrrole, pyrazole and triazole derivatives disclosed in U.S. Pat. No. 5,183,899, EP-323841, EP-409332 and JP-A-1-287071 and the like, benzimidazole derivatives disclosed in U.S. Pat. No. 4,880,804, EP-0392317, EP-0399732, EP-0400835, EP-425921, EP-459136 and JP-A-3-63264 and the like, azaindene derivatives disclosed in EP-399731 and the like, pyrimidone derivatives disclosed in EP-407342 and the like, quinazoline derivatives disclosed in EP-411766 and the like, xanthine derivatives disclosed in EP-430300 and the like, condensed imidazole derivatives disclosed in EP-434038 and the like, pyrimidinedione derivatives disclosed in EP-442473 and the like, thienopyridone derivatives disclosed in EP-443568 as well as heterocyclic compounds disclosed in EP-445811, EP-483683, EP-518033, EP-520423, EP-588299, EP-603712 and the like. Among those listed above, representative compounds are found also in Journal of Medicinal Chemistry, Vol. 39, No. 3, p. 625–656, 1996. A non-peptide heterocyclic compound having an angiotensin II antagonistic activity may also be any other nonpeptidic heterocyclic compound having an angiotensin II antagonistic activity than the compounds found in the reference describe above, and those employed preferably are losartan (DuP753), eprosartan (SK&F108566), candesartan cilexetil (TCV-116), telmisartan (BIBR277), irbesartan (SR47436), tasosartan (ANA-756), olmesartan and metabolically activated substances thereof (such as candesartan).

As a heterocyclic compound having an angiotensin II antagonistic activity, a benzimidazole derivative represented by the formula (I):

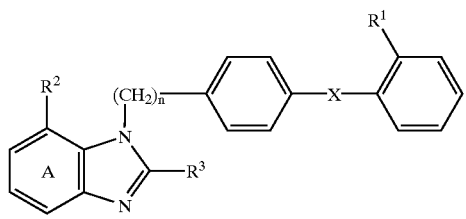

(I)

wherein $R^1$ is a group capable of forming an anion or a group capable of being converted into such a group, X denotes that a phenylene group and a phenyl group are bound directly or through a spacer having 2 or less of atomic chains, n is an integer of 1 or 2, ring A is a further optionally substituted benzene ring, $R^2$ is a group capable of forming an anion or a group capable of being converted into such a group, $R^3$ is an optionally substituted hydrocarbon residue which may be bound through a heteroatom (preferably an optionally substituted hydrocarbon residue bound through an oxygen atom) or its salt is employed preferably.

In the formula above, the group represented by $R^1$ which is capable of forming an anion (group having a hydrogen atom capable of being released as a proton) may for example be (1) a carboxyl group, (2) a tetrazolyl group, (3) a trifluoromethanesulfonamide group ($-NHSO_2CF_3$), (4) a phosphoric acid group, (6) a sulfonic acid group, (6) a 5- to 7-membered (preferably 5- to 6-membered), monocyclic, optionally substituted heterocyclic residue containing one or more than two heteroatoms selected from N, S and O.

A "5- to 7-membered (preferably 5- to 6-membered), monocyclic, optionally substituted heterocyclic residue containing one or more than two heteroatoms selected from N, S and O" described above may for example be:

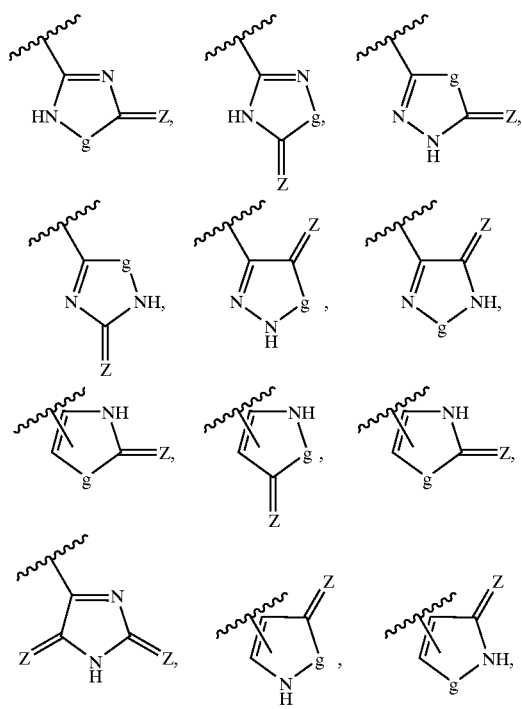

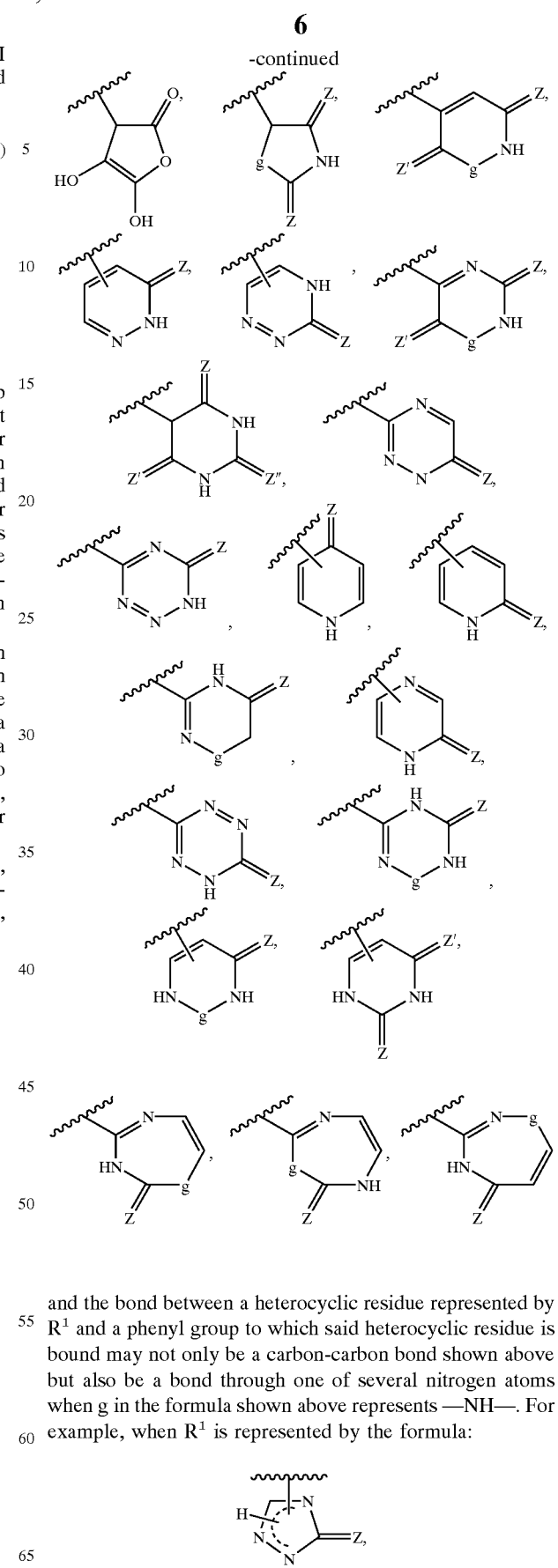

and the bond between a heterocyclic residue represented by $R^1$ and a phenyl group to which said heterocyclic residue is bound may not only be a carbon-carbon bond shown above but also be a bond through one of several nitrogen atoms when g in the formula shown above represents —NH—. For example, when $R^1$ is represented by the formula:

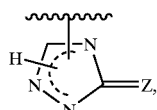

the following types of bond:

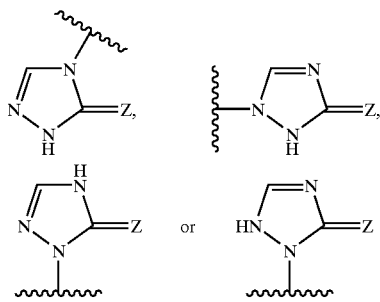

are specifically included. Other nitrogen atom-mediated bonds include those represented by the formulae:

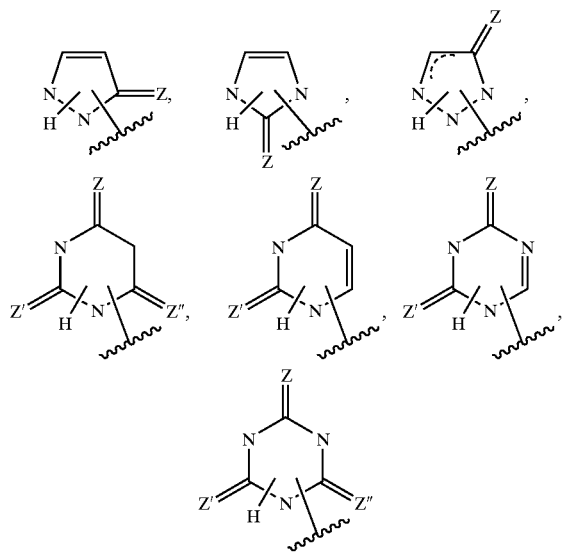

In the formulae above, g is —CH$_2$—, —NH—, —O— or —S(O)m, and each of >=Z, >=Z' and >=Z" is a carbonyl group, thiocarbonyl group or an optionally oxidized sulfur atom respectively (e.g., S, S(O), S(O)$_2$ and the like) (preferably carbonyl or thiocarbonyl group, more preferably carbonyl group), and m is an integer of 0, 1 or 2.

Preferably a heterocyclic residue represented by R$^1$ may for example be a group having an —NH— or —OH group as a proton donor together with a carbonyl group, thiocarbonyl group or sulfinyl group as a proton acceptor such as an oxadiazolone ring, oxadiazolothione ring or thiadiazolone ring. Further the heterocyclic residue represented by R$^1$ may be taken together with a cyclic substituent to form a condensed ring, in that case the heterocyclic residue represented by R$^1$ is preferably a 5- to 6-membered ring residue, more preferably a 5-membered ring residue.

A heterocyclic residue represented by R$^1$ is preferably a group represented by the formula:

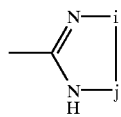

wherein i is —O— or —S—, j is >=O, >=S or >=S(O)m, and m is defined as described above (those preferred being 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl, especially, 2,5-dihydro-5-oxo-1,2,4-oxadiazol-3-yl).

A heterocyclic residue (R$^1$) described above is present as a tautomeric form as shown below. For example, when Z=O and g=O in the formula:

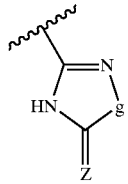

then three tautomeric forms a', b' and c' represented by the formulae:

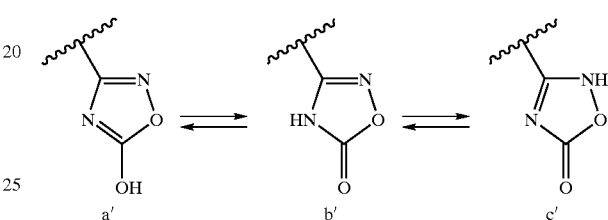

are present, and a heterocyclic residue represented by the formula:

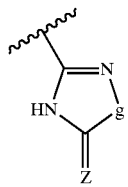

is understood to include all of a', b' and c' shown above.

The group represented by R$^1$ which is capable of forming an anion may be protected at a substitutable position by an optionally substituted lower (C$_{1-4}$) alkyl group or acyl group (e.g., lower (C$_{2-5}$) alkanoyl, benzoyl) and the like.

An optionally substituted lower (C$_{1-4}$) alkyl group may include, for example, (1) a lower (C$_{1-4}$) alkyl group which may be substituted by 1 to 3 phenyl groups which may have a halogen atom, nitro, lower (C$_{1-4}$) alkyl, lower (C$_{1-4}$) alkoxy and the like (e.g., methyl, triphenylmethyl, p-methoxybenzyl, p-nitrobenzyl), (2) a lower (C$_{1-4}$) alkoxy-lower (C$_{1-4}$) alkyl group (e.g., methoxymethyl, ethoxymethy), and (3) a group represented by the formula: —CH(R$^4$)—OCOR$^5$ [wherein R$^4$ is (a) hydrogen, (b) a straight or branched lower alkyl group having 1 to 6 carbon atoms (e.g., methyl, ethyl, n-propyl, isopropyl, n-butyl, isobutyl, t-butyl, n-pentyl, isopentyl, neopentyl), (c) a straight or branched lower alkenyl group having 2 to 6 carbon atoms or (d) a cycloalkyl group having 3 to 8 carbon atoms (e.g., cyclopentyl, cyclohexyl, cycloheptyl), and R$^5$ is (a) a straight or branched lower alkyl group having 1 to 6 carbon atoms (e.g., methyl, ethyl, n-propyl, isopropyl, n-butyl, isobutyl, sec-butyl, t-butyl, n-pentyl, isopentyl, neopentyl), (b) a straight or branched lower alkenyl group having 2 to 6 carbon atoms, (c) a lower alkyl group having 1 to 3 carbon atoms which is substituted by a cycloalkyl group having 3 to 8 carbon atoms (e.g., cyclopentyl, cyclohexyl, cycloheptyl) or an optionally substituted aryl group (e.g., phenyl or naphthyl group which may have a halogen atom, nitro, lower ($C_{1-4}$) alkyl, lower ($C_{1-4}$) alkoxy) (e.g., benzyl, p-chlorobenzyl, phenethyl, cyclopentyl-methyl, cyclohexylmethyl), (d) a lower alkenyl group having 2 to 3 carbon atoms which is substituted by a cycloalkyl having 3 to 8 carbon atoms or an optionally substituted aryl group (e.g., phenyl or naphthyl group which may have a halogen atom, nitro, lower ($C_{1-4}$) alkyl, lower ($C_{1-4}$) alkoxy) (e.g., group having alkenyl moiety such as vinyl, propenyl, allyl, isopropenyl, including cinnamyl), (e) an optionally substituted aryl group (e.g., phenyl or naphthyl group which may have a halogen atom, nitro, lower ($C_{1-4}$) alkyl, lower ($C_{1-4}$) alkoxy, including phenyl, p-tolyl, naphthyl), (f) a straight or branched lower alkoxy group having 1 to 6 carbon atoms (e.g., methoxy, ethoxy, n-propoxy, isopropoxy, n-butoxy, isobutoxy, sec-butoxy, t-butoxy, n-pentyloxy, isopentyloxy, neopentyloxy), (g) a straight or branched lower alkenyloxy group having 2 to 8 carbon atoms (e.g., allyloxy, isobutenyloxy),(h) a cycloalkyloxy group having 3 to 8 carbon atoms (e.g., cyclopentyloxy, cyclohexyloxy, cycloheptyloxy), (i) a lower alkoxy group having 1 to 3 carbon atoms which is substituted by a cycloalkyl having 3 to 8 carbon atoms (e.g., cyclopentyl, cyclohexyl, cyclobutyl) or an optionally substituted aryl group (e.g., phenyl or naphthyl group which may have a halogen atom, nitro, lower ($C_{1-4}$) alkyl, lower ($C_{1-4}$) alkoxy), (e.g., group having an alkoxy moiety such as methoxy, ethoxy, n-propoxy and isopropoxy, including benzyloxy, phenethyloxy, cyclopentylmethoxy, cyclohexylmethoxy), (j) a lower alkenyloxy group having 2 to 3 carbon atoms which is substituted by a cycloalkyl having 3 to 8 carbon atoms (e.g., cyclopentyl, cyclohexyl, cycloheptyl) or an optionally substituted aryl group (e.g., phenyl or naphthyl group which may have a halogen atom, nitro, lower ($C_{1-4}$) alkyl, lower ($C_{1-4}$) alkoxy)) (e.g., group having an alkenyloxy moiety such as vinyloxy, propenyloxy, allyloxy and isopropenyloxy, including cinnamyloxy) or (k) an optionally substituted aryloxy group (e.g., phenoxy or naphthoxy group which may have a halogen atom, nitro, lower ($C_{1-4}$) alkyl and lower ($C_{1-4}$) alkoxy, including phenoxy, p-nitrophenoxy, naphthoxy).

The group represented by $R^1$ which is capable of forming an anion may have, in addition to the protective groups described above such as an optionally substituted lower ($C_{1-4}$) alkyl group or acyl group (e.g., lower ($C_{1-5}$) alkanoyl, benzoyl), a further substituent group such as an optionally substituted lower ($C_{1-4}$) alkyl (for example, one similar to an "optionally substituted lower ($C_{1-4}$) alkyl group" exemplified above as a protective group for the group represented by $R^1$ which is capable of forming an anion), halogen atom, nitro, cyano, lower ($C_{1-4}$) alkoxy, and amino which may be substituted by one or two lower ($C_{1-4}$) alkyls.

In the formula above, the group represented by $R^1$ which is capable of forming an anion (group having a hydrogen atom capable of being released as a proton) may be a group capable of being converted into a group capable of forming an anion under a biological, i.e., physiological condition (for example, as a result of an in vivo reaction such as oxidation, reduction or hydrolysis by an intravital enzyme) (i.e., prodrug), or may be a group capable of being converted into a group capable of forming an anion represented by $R^1$ as a result of a chemical reaction (i.e., synthetic intermediate), such as cyano, N-hydroxycarbamimidoyl group (—C(=N—OH)—NH$_2$) and the groups (1)~(6) below which is protected by an optionally substituted lower ($C_{1-4}$) alkyl group or acyl group; (1) a carboxyl group, (2) a tetrazolyl group, (3) a trifluoromethanesulfonamide group(—NHSO$_2$CF$_3$), (4) a phosphoric acid group, (5) a sulfonic acid group and (6) a 5- to 7-membered (preferably 5- to 6-membered), monocyclic, optionally substituted heterocyclic residue containing one or more than two heteroatoms selected from N, S and O.

$R^1$ is preferably carboxyl, tetrazolyl or 2,5-dihydro-5-oxo-1,2,4-oxadiazol-3-yl (preferably tetrazolyl), which may be protected by an optionally substituted lower ($C_{1-4}$) alkyl (e.g., methyl, triphenylmethyl, methoxymethyl, ethoxymethyl, p-methoxybenzyl, p-nitrobenzyl) or acyl group (e.g., lower ($C_{2-5}$) alkanoyl, benzoyl), or cyano, N-hydroxycarbamimidoyl (preferably cyano), and especially preferably tetrazolyl is used.

In the formula above, X denotes that adjacent phenylene group and phenyl group are bound directly or through a spacer having 2 or less of atomic chains (preferably a direct bond), and such a spacer having 2 or less of atomic chains may be any divalent chain whose number of the atoms constituting the straight chain moiety is 1 or 2 and which may have a side chain. Those exemplified typically are a lower ($C_{1-4}$) alkylene whose number of the atoms constituting the straight chain moiety is 1 or 2, —CO—, —O—, —S—, —NH—, —CO—NH—, —O—CH$_2$—, —S—CH$_2$—, —CH=CH— and the like.

In the formula above, n is an integer of 1 or 2 (preferably 1).

In the formula above, ring A is a benzene ring which may have a further substituent group in addition to the substituent $R^2$, and such a substituent group may include, for example, (1) a halogen (e.g., F, Cl, Br), (2) a cyano, (3) a nitro, (4) an optionally substituted lower ($C_{1-4}$) alkyl, (5) a lower ($C_{1-4}$) alkoxy, (6) an optionally substituted amino group (e.g., amino, N-lower ($C_{1-4}$) alkylamino (e.g., methylamino), N,N-di lower ($C_{1-4}$) alkylamino (e.g., dimethylamino), N-arylamino (e.g., phenylamino), alicyclic amino (e.g., morpholino, piperidino, piperazino, N-phenylpiperadino)), (7) a group represented by the formula: —CO-D' [wherein D' is a hydroxyl group or a lower ($C_{1-4}$) alkoxy whose alkyl moiety may be substituted by a hydroxyl group, lower ($C_{1-4}$) alkoxy, lower ($C_{2-6}$) alkanoyloxy (e.g., acetoxy, pivaloyloxy), lower ($C_{1-6}$) alkoxycarbonyloxy (e.g., methoxycarbonyloxy, ethoxycarbonyloxy) or lower ($C_{3-6}$) cycloalkoxycarbonyloxy (e.g., cyclohexyloxycarbonyloxy), or (8) tetrazolyl, trifluoromethanesulfonamide group, phosphoric acid group or sulfonic acid group which may be protected by an optionally substituted lower ($C_{1-4}$) alkyl (for example, one similar to an "optionally substituted lower ($C_{1-4}$) alkyl group" exemplified above as a protective group for a group as $R^1$ which is capable of forming an anion) or acyl (e.g., lower ($C_{2-5}$) alkanoyl, benzoyl).

While 1 to 2 substituent groups listed above may occur simultaneously in the substitutable position on a benzene ring, a further substituent group, other than the substituent $R^2$, which may be possessed by the ring A is preferably an optionally substituted lower ($C_{1-4}$) alkyl (e.g., a lower ($C_{1-4}$) alkyl group which may be optionally substituted by a hydroxyl group, carboxyl group, halogen) and a halogen, and more preferably the ring A does not have any substituent group other than the substituent $R^2$.

In the formula above, the group represented by $R^2$ which is capable of forming an anion (group having a hydrogen atom capable of being released as a proton) may include, for example, (1) an optionally esterified or amidated carboxyl group, (2) a tetrazolyl group, (3) a trifluoromethanesulfonamide group (—NHSO$_2$CF$_3$), (4) a phosphoric acid group, (5) a sulfonic acid group, and any of these groups may be protected by an optionally substituted lower alkyl group (for example, one similar to an "optionally substituted lower ($C_{1-4}$) alkyl group" exemplified above as a protective group for the group represented by $R^1$ which is capable of forming an anion) or acyl group (e.g., lower ($C_{2-5}$) alkanoyl, benzoyl), and may be any group capable of forming an anion or capable of being converted into such a group under a biological, i.e., physiological condition (for example, as a result of an in vivo reaction such as oxidation, reduction or hydrolysis by an intravital enzyme) or as a result of a chemical reaction. An optionally esterified or amidated carboxyl represented by $R^2$ may include, for example, a group represented by the formula: —CO-D—[wherein D is (1) a hydroxyl group, (2) an optionally substituted amino (e.g., amino, N-lower ($C_{1-4}$) alkylamino, N,N-di-lower ($C_{1-4}$) alkylamino) or (3) an optionally substituted alkoxy {e.g., (i) a lower ($C_{1-6}$) alkoxy group whose alkyl moiety may be substituted by a hydroxyl group, an optionally substituted amino (e.g., amino, N-lower ($C_{1-4}$) alkylamino, N,N-di-lower ($C_{1-4}$) alkylamino, piperidino, morpholino), halogen, lower ($C_{1-6}$) alkoxy, lower ($C_{1-6}$) alkylthio, lower ($C_{3-8}$) cycloalkoxy or an optionally substituted dioxolenyl (e.g., 5-methyl-2-oxo-1,3-dioxolen-4-yl), or (ii) a group represented by the formula: —O—CH($R^6$)—OCOR$^7$—[wherein $R^6$ is (a) hydrogen, (b) a straight or branched lower alkyl group having 1 to 6 carbon atoms (e.g., methyl, ethyl, n-propyl, isopropyl, n-butyl, isobutyl, t-butyl, n-pentyl, isopentyl, neopentyl), (c) a straight or branched lower alkenyl group having 2 to 6 carbon atoms or (d) a cycloalkyl group having 3 to 8 carbon atoms (e.g., cyclopentyl, cyclohexyl, cycloheptyl), and $R^7$ is (a) a straight or branched lower alkyl group having 1 to 6 carbon atoms (e.g., methyl, ethyl, n-propyl, isopropyl, n-butyl, isobutyl, sec-butyl, t-butyl, n-pentyl, isopentyl, neopentyl), (b) a straight or branched lower alkenyl group having 2 to 6 carbon atoms, (c) a lower alkyl group having 1 to 3 carbon atoms which is substituted by a cycloalkyl group having 3 to 8 carbon atoms (e.g., cyclopentyl, cyclohexyl, cycloheptyl) or an optionally substituted aryl group (e.g., phenyl or naphthyl group which may have a halogen atom, nitro, lower ($C_{1-4}$) alkyl, lower ($C_{1-4}$) alkoxy) (e.g., benzyl, p-chlorobenzyl, phenethyl, cyclopentylmethyl, cyclohexylmethyl), (d) a lower alkenyl group having 2 to 3 carbon atoms which is substituted by a cycloalkyl having 3 to 8 carbon atoms or an optionally substituted aryl group (e.g., phenyl or naphthyl group which may have a halogen atom, nitro, lower ($C_{1-4}$) alkyl, lower ($C_{1-4}$) alkoxy) (e.g., group having alkenyl moiety such as vinyl, propenyl, allyl, isopropenyl, including cinnamyl), (e) an optionally substituted aryl group (e.g., phenyl or naphthyl group which may have a halogen atom, nitro, lower ($C_{1-4}$) alkyl, lower ($C_{1-4}$) alkoxy, including phenyl, p-tolyl, naphthyl), (f) a straight or branched lower alkoxy group having 1 to 6 carbon atoms (e.g., methoxy, ethoxy, n-propoxy, isopropoxy, n-butoxy, isobutoxy, sec-butoxy, t-butoxy, n-pentyloxy, isopentyloxy, neopentyloxy), (g) a straight or branched lower alkenyloxy group having 2 to 8 carbon atoms (e.g., allyloxy, isobutenyloxy),(h) a cycloalkyloxy group having 3 to 8 carbon atoms (e.g., cyclopentyloxy, cyclohexyloxy, cycloheptyloxy), (i) a lower alkoxy group having 1 to 3 carbon atoms which is substituted by a cycloalkyl having 3 to 8 carbon atoms (e.g., cyclopentyl, cyclohexyl, cycloheptyl) or an optionally substituted aryl group (e.g., phenyl or naphthyl group which may have a halogen atom, nitro, lower ($C_{1-4}$) alkyl, lower ($C_{1-4}$) alkoxy), (e.g., group having an alkoxy moiety such as methoxy, ethoxy, n-propoxy and isopropoxy, including benzyloxy, phenethyloxy, cyclopentylmethoxy, cyclohexylmethoxy), (j) a lower alkenyloxy group having 2 to 3 carbon atoms which is substituted by a cycloalkyl having 3 to 8 carbon atoms (e.g., cyclopentyl, cyclohexyl, cycloheptyl) or an optionally substituted aryl group (e.g., phenyl or naphthyl group which may have a halogen atom, nitro, lower ($C_{1-4}$) alkyl, lower ($C_{1-4}$) alkoxy)) (e.g., group having an alkenyloxy moiety such as vinyloxy, propenyloxy, allyloxy and isopropenyloxy, including cinnamyloxy) or (k) an optionally substituted aryloxy group (e.g., phenoxy or naphthoxy group which may have a halogen atom, nitro, lower ($C_{1-4}$) alkyl and lower ($C_{1-4}$)alkoxy, including phenoxy, p-nitrophenoxy, naphthoxy)]}].

As $R^2$, an optionally esterified carboxyl is preferred and those exemplified typically are —COOH and its salt, —COOMe, —COOEt, —COOtBu, —COOPr, pivaloyloxymethoxycarbonyl, 1-(cyclohexyloxy-carbonyloxy)ethoxycarbonyl, 5-methyl-2-oxo-1,3-dioxolen-4-ylmethoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl and the like, and may be any group capable of forming an anion (e.g., COO$^-$ or its derivatives) or capable of being converted into such a group under a biological, i.e., physiological condition (for example, as a result of an in vivo reaction such as oxidation, reduction or hydrolysis by an in vivo enzyme) or as a result of a chemical reaction, and also may be a carboxyl group or its prodrugs.

As $R^2$ described above, a group represented by the formula: —CO-D[wherein D is (1) a hydroxyl group or (2) a lower ($C_{1-4}$) alkoxy group whose alkyl moiety may be substituted by a hydroxyl group, amino, halogen, lower ($C_{2-6}$) alkanoyloxy (e.g., acetoxy, pivaloyloxy), lower ($C_{3-8}$) cycloalkanoyloxy, lower ($C_{1-6}$) alkoxycarbonyloxy (e.g., methoxycarbonyloxy, ethoxycarbonyloxy), lower ($C_{3-8}$) cycloalkoxycarbonyloxy (e.g., cyclohexyloxycarbonyloxy), lower ($C_{1-4}$) alkoxy or lower ($C_{3-8}$) cycloalkoxy] is preferred, among which a carboxyl which is esterified with a lower ($C_{1-4}$) alkyl (preferably, methyl or ethyl) is especially preferred.

In the formula above, a "hydrocarbon residue" in an "optionally substituted hydrocarbon residue which may be bound through a heteroatom" represented by $R^3$ may include, for example, (1) an alkyl group, (2) an alkenyl group, (3) an alkynyl group, (4) a cycloalkyl group, (5) an aryl group, (6) an aralkyl group and the like, among which an alkyl group, alkenyl group and cycloalkyl group is preferred.

An alkyl group of (1) described above may be a straight or branched lower alkyl group having about 1 to 8 carbon atoms, for example, methyl, ethyl, propyl, isopropyl, butyl, isobutyl, sec-butyl, t-butyl, pentyl, i-pentyl, hexyl, heptyl, octyl and the like.

An alkenyl group of (2) described above may be a straight or branched lower alkenyl group having about 2 to 8 carbon atoms, for example, vinyl, propenyl, 2-butenyl, 3-butenyl, isobutenyl, 2-octenyl and the like.

An alkynyl group of (3) described above may be a straight or branched lower alkynyl group having about 2 to 8 carbon atoms, for example, ethynyl, 2-propynyl, 2-butynyl, 2-pentynyl, 2-octynyl and the like.

A cycloalkyl group of (4) described above may be a lower cycloalkyl having about 3 to 6 carbon atoms, for example, cyclopropyl, cyclobutyl, cyclopentyl, cyclohexyl and the like.

Any of the alkyl groups, alkenyl groups, alkynyl groups or cycloalkyl groups described above may be substituted by a hydroxyl group, optionally substituted amino group (e.g., amino, N-lower ($C_{1-4}$) alkylamino, N,N-di-lower ($C_{1-4}$) alkylamino), halogen, lower ($C_{1-4}$) alkoxy group, lower ($C_{1-4}$) alkylthio group and the like.

An aralkyl group of (5) described above may for example be a phenyl-lower ($C_{1-4}$) alkyl such as benzyl and phenethyl, while an aryl group of (6) described above may for example be phenyl.

An aralkyl group or aryl group described above may have, in any position of its benzene ring, for example, a halogen (e.g., F, Cl, Br), nitro, optionally substituted amino group (e.g., amino, N-lower ($C_{1-4}$) alkylamino, N,N-di-lower ($C_{1-4}$) alkylamino), lower ($C_{1-4}$) alkoxy (e.g., methoxy, ethoxy), lower ($C_{1-4}$) alkylthio (e.g., methylthio, ethylthio), lower ($C_{1-4}$) alkyl (e.g., methyl, ethyl).

Among those listed above, a "hydrocarbon residue" in an "optionally substituted hydrocarbon residue which may be bound through a heteroatom" represented by $R^3$ is preferably an optionally substituted alkyl or alkenyl group (e.g., a lower ($C_{1-5}$) alkyl or lower ($C_{2-5}$) alkenyl group which may be substituted by a hydroxyl group, amino group, halogen or lower ($C_{1-4}$) alkoxy group), among which a lower ($C_{1-5}$) alkyl (more preferably ethyl) is especially preferred.

A "heteroatom" in an "optionally substituted hydrocarbon residue which may be bound through a heteroatom" represented by $R^3$ may include, for example, —O—, —S(O)$_m$— [m is an integer of 0 to 2], —NR'— [R' is a hydrogen atom or a lower ($C_{1-4}$) alkyl], among which —O— is preferred especially.

Among those listed above, $R^3$ is preferably a lower ($C_{1-5}$) alkyl or lower ($C_{2-5}$) alkenyl group which may be bound through —O—, —S(O)$_m$— [m is an integer of 0 to 2] or —NR'— [R' is a hydrogen atom or lower ($C_{1-4}$) alkyl] and which may be substituted by a substituent group selected from a hydroxy group, amino group, halogen and lower ($C_{1-4}$) alkoxy group, more preferably a lower ($C_{1-5}$) alkyl or lower ($C_{1-5}$) alkoxy (especially ethoxy).

Among heterocyclic compounds represented by the formula (I) having an angiotensin II antagonistic activity, a benzimidazole-7-carboxylic acid derivative represented by the formula (I)':

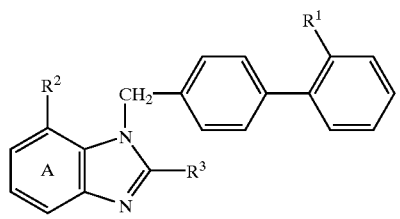

(I')

wherein $R^1$ is (1) a carboxyl group, (2) a tetrazolyl group, or (3) a group represented by the formula:

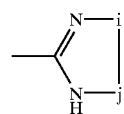

wherein i is —O— or —S—, j is >=O, >=S or >=S(O)$_m$, and m is defined as described above, ring A is a benzene ring which may be substituted by an optionally substituted lower ($C_{1-4}$) alkyl (e.g., lower ($C_{1-4}$) alkyl which may be substituted by a hydroxyl group, carboxyl group or halogen) or halogen in addition to the substituent $R^2$ (preferably a benzene ring which does not have any substituent group other than the substituent $R^2$), $R^2$ is a group represented by the formula:—CO-D [wherein D is (1) a hydroxyl group or (2) a lower ($C_{1-4}$) alkoxy group whose alkyl moiety may be substituted by a hydroxyl group, amino, halogen, lower ($C_{2-6}$) alkanoyloxy (e.g., acetoxy, pivaloyloxy), lower ($C_{3-8}$) cycloalkanoyloxy, lower ($C_{1-6}$) alkoxycarbonyloxy (e.g., methoxycarbonyloxy, ethoxycarbonyloxy), lower ($C_{3-8}$) cycloalkoxycarbonyloxy (e.g., cyclohexyloxycarbonyloxy), lower ($C_{1-4}$) alkoxy or lower ($C_{3-8}$) cycloalkoxy], $R^3$ is a lower ($C_{1-5}$) alkyl or lower ($C_{2-5}$) alkenyl group which may be bound through —O—, —S(O)$_m$— [m is an integer of 0 to 2] or —NR'— [R' is a hydrogen atom or lower ($C_{1-4}$) alkyl] and which may be substituted by a substituent group selected from a hydroxy group, amino group, halogen and lower ($C_{1-4}$) alkoxy group (preferably a lower ($C_{1-5}$) alkyl or lower ($C_{1-5}$) alkoxy; more preferably ethoxy), or a pharmacologically acceptable salt thereof is preferable, among which 2-ethoxy-1-[[2'-(1H-tetrazol-5-yl)biphenyl-4-yl]methyl]benzimidazole-7-carboxylic acid [candesartan], 1-(cyclohexyloxycarbonyloxy)ethyl 2-ethoxy-1-[[2'-(1H-tetrazol-5-yl)biphenyl-4-yl]methyl]benzimidazole-7-carboxylate [candesartan cilexetil], pivaloyloxymethyl 2-ethoxy-1-[[2'-(1H-tetrazol-5-yl)biphenyl-4-yl]methyl]benzimidazole-7-carboxylate, 2-ethoxy-1-[[2'-(2,5-dihydro-5-oxo-1,2,4-oxadiazol-3-yl)biphenyl-4-yl]methyl]benzimidazole-7-carboxylic acid or salts thereof are particularly preferable.

Any of the benzimidazole derivatives described above can be prepared by a known method such as those described for example in EP-425921, EP-459136, EP-553879, EP-578125, EP-520423, EP-668272 or methods analogous thereto. When candesartan cilexetil is employed, it is preferable to use a stable C-form crystal described in EP-459136.

A heterocyclic compound having an angiotensin II antagonistic activity employed in the present invention or its prodrug may be itself or in the form of its pharmacologically acceptable salt. Such salt, when said heterocyclic compound having an angiotensin II antagonistic activity has an acidic group such as a carboxyl group, may include for example a salt with an inorganic base (e.g., alkaline metals such as sodium and potassium, alkaline earth metals such as calcium and magnesium, transition metals such as zinc, iron and copper) or an organic base (e.g., organic amines such as trimethylamine, triethylamine, pyridine, picoline, ethanolamine, diethanolamine, triethanolamine, dicyclohexylamine and N,N'-dibenzylethylenediamine, basic amino acids such as arginine, lysine and ornithine).

When a heterocyclic compound having an angiotensin II antagonistic activity has a basic group such as an amino group, salt with an inorganic acid or an organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid) or with an acidic amino acid such as aspartic acid and glutamic acid can be exemplified.

A prodrug of a heterocyclic compound having an angiotensin II antagonistic activity employed in the present invention [hereinafter referred to as AII-antagonizing compound] is a compound which is converted into an AII-antagonizing compound as a result of a reaction with an enzyme or gastric acid under an in vivo physiological condition, i.e., a compound which undergoes an enzymatic oxidation, reduction or hydrolysis to be converted into an AII-antagonizing compound, a compound which undergoes a hydrolysis by gastric acid to be converted into an AII-antagonizing compound. A prodrug of an AII-antagonizing compound may include, for example, a compound formed as a result of the acylation, alkylation or phosphorylation of an amino group of the AII-antagonizing compound (e.g., a compound formed as a result of the eicosanoylation, alanylation, pentylaminocarbonylation, (5-mehtyl-2-oxo-1,3-dioxolen-4-yl)methoxycarbonylation, tetrahydrofuranylation, pyrrolidylmethylation, pivaloyloxymethylation, tert-butylation of an amino group of the AII-antagonizing compound); a compound formed as a result of the acylation, alkylation, phosphorylation or boration of a hydroxyl group of the AII-antagonizing compound (e.g., a compound formed as a result of the acetylation, palmitoylation, propanoylation, pivaloylation, succinylation, fumarylation, alanylation, dimethylaminomethylcarbonylation of a hydroxyl group of the AII-antagonizing compound); and a compound formed as a result of the esterification or amidation of a carboxyl group of the AII-antagonizing compound (e.g., a compound formed as a result of the ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxy-carbonyloxyethyl-esterification and methylamidation of a carboxyl group of the AII-antagonizing compound) and the like. Any of these compounds can be produced from an AII-antagonizing compound by a method known per se.

A prodrug of an AII-antagonizing compound may be a compound which is converted into an AII-antagonizing compound under a physiological condition such as those described in "IYAKUHINNOKAIHATSU (Pharmaceutical development), Vol.7, Molecular designing, p163 to 198, published in 1990 by HIROKAWASHOTEN.

An AII-antagonizing compound may be a hydrate or anhydride.

A heterocyclic compound having an angiotensin II antagonistic activity employed in the present invention or a pharmaceutically acceptable salt thereof has a low toxicity, and can be administered as a TNF-α inhibitor, as it is or in the form of a pharmaceutical composition as a mixture with a pharmaceutically acceptable carrier, to a mammal (e.g., human, mouse, rat, rabbit, dog, cat, cattle, horse, pig, monkey and the like).

A pharmacologically acceptable carrier employed here may be any of various organic and inorganic carriers customarily used as a pharmaceutical material, such as an excipient, lubricant, binder and disintegrant for a solid formulation; a solvent, solubilizer, suspending agent, osmotic agent, buffering agent and pain-suppressing agent for a liquid formulation. A pharmaceutical additives such as a preservative, antioxidant, coloring agent and sweetener can also be used if necessary.

Preferable examples of the excipient include for example lactose, sugar, D-mannitol, D-sorbitol, starch, α-starch, dextrin, crystalline cellulose, low-substituted hydroxypropylcellulose, carboxymethylcellulose sodium, gum arabic, dextrin, pullulan, light anhydrous silicic acid, synthetic aluminum silicate, magnesium aluminate metha-silicate and the like.

Preferable examples of the lubricant include, for example, magnesium stearate, calcium stearate, talc, colloidal silica and the like.

Preferable examples of the binder include, for example, α-starch, sucrose, gelatin, gum arabic, methylcellulose, carboxymethylcellulose, carboxymethylcellulose sodium, crystalline cellulose, sugar, D-mannitol, trehalose, dextrin, pullulan, hydroxypropylcellulose, hydroxypropyl-methylcellulose, polyvinylpyrrolidone and the like.

Preferable examples of the disintegrant include, for example, lactose, sugar, starch, carboxymethyl cellulose, carboxymethylcellulose calcium, croscarmellose sodium, carboxymethyl starch sodium, light anhydrous silicic acid, low-substituted hydroxypropylcellulose and the like.

Preferable examples of the solvent include, for example, water for injection, physiological saline, Linger's solution, alcohol, propylene glycol, polyethylene glycol, sesame oil, corn oil, olive oil, cottonseed oil and the like.

Preferable examples of the solubilizing agent include, for example, polyethylene glycol, propylene glycol, D-mannitol, trehalose, benzyl benzoate, ethanol, tris-aminomethane, cholesterol, triethanolamine, sodium carbonate, sodium citrate, sodium salicylate, sodium acetate and the like.

Preferable examples of the suspending agent include, for example, a surfactant such as stearyltriethanolamine, sodium laurylsulfate, laurylaminopropionic acid, lecithin, benzalkonium chloride, benzethonium chloride, glycerin monostearate and the like; a hydrophilic polymer such as polyvinylalcohol, polyvinylpyrrolidone, carboxymethylcel-lulose sodium, methylcellulose, hydroxymethylcellulose, hydroxyethylcellulose, hydroxypropylcellulose and the like; a polysolvate and a polyoxyethylene hardened castor oil and the like.

Preferable examples of the osmotic agent include, for example, sodium chloride, glycerin, D-mannitol, D-sorbitol, glucose and the like.

Preferable examples of the buffering agent include, for example, a buffer solution of a phosphate, acetate, carbonate, citrate and the like.

Preferable examples of the pain-suppressing agent include, for example, benzyl alcohol and the like.

Preferable examples of the preservative include, for example, a p-oxybenzoate, chlorobutanol, benzylalcohol, phenethylalcohol, dehydroacetic acid, sorbic acid and the like.

Preferable examples of the antioxidant include, for example, sulfite, ascorbate and the like.

Preferable examples of the colorant include, for example, a water-soluble edible tar dye (e.g., edible dyes such as edible red No.2 and No.3, edible yellow No.4 and No.5, edible blue No.1 and No.2), a water-insoluble lake dye (e.g., an aluminum salt of a water-soluble edible tar dye described above), a naturally-occurring dye (e.g., β-carotine, chlorophyll, colcothar) and the like.

Preferable examples of the sweetener include, for example, saccharin sodium, dipotassisum glycyrrhetinate, aspartame, stevioside and the like.

The formulation of the pharmaceutical composition include, for example, an oral formulation such as tablet, capsule (including soft capsule, microcapsule), granule, powder, syrup, emulsion, suspension and the like; and a parenteral formulation such as a injection (e.g., subcutaneous injection, intravenous injection, intramuscular injection, intraperitoneal injection, intravitreous injection), infusion formulation, external formulation (e.g., nasal formulation, percutaneous formulation, ointment), suppository (e.g., rectal suppository, vaginal suppository), pellet, dripping formulation and the like, which can safely be administered through an oral or parenteral route.

A pharmaceutical composition can be produced by a method used customarily in the field of pharmaceutical preparation, for example, by a method described in Japanese Pharmacopoeia. A typical method for producing a pharmaceutical preparation is detailed below.

For example, an oral formulation is produced by adding an excipient (e.g., lactose, sugar, starch, D-mannitol), disintegrant (e.g., carboxymethylcellulose calcium), binder (e.g., α-starch, gum arabic, carboxymethylcellulose, hydroxypropylcellulose, polyvinylpyrrolidone) and lubricant (e.g., talc, magnesium stearate, polyethylene glycol 6000) to an active ingredient, and compressing to shape and then, if necessary, coating with a coating base by a method known per se for the purpose of masking of a taste, enteric dissolution performance or sustained release.

Said coating base include, for example, a sugar coating base, water-soluble film coating base, enteric film coating base, sustained release film coating base and the like.

As a sugar coating base, a sugar is used, and also may be used in combination with one or more kind of base selected from talc, precipitated calcium carbonate, gelatin, gum arabic, pullulan, carnauba wax and the like.

A water-soluble film coating base include, for example, a cellulose-based polymer such as hydroxypropylcellulose, hydroxypropylmethylcellulose, hydroxyethylcellulose, methylhydroxyethylcellulose and the like; a synthetic polymer such as polyvinylacetal diethylaminoacetate, aminoalkylmethacrylate copolymer E [Eudragit E, (trade name), Rohm Pharma], a polyvinylpyrrolidone; a polysaccharide such as pullulan and the like.

An enteric film coating base include, for example, a cellulose-based polymer such as hydroxypropylmethylcellulose phthalate, hydroxypropylmethylcellulose acetate succinate, carboxymethylethylcellulose, cellulose acetate phthalate and the like; an acrylic acid-based polymer such as methacrylic acid copolymer L [Eudragit L (trade name), Rohm Pharma], methacrylic acid copolymer LD [Eudragit L-30D55 (trade name), Rohm Pharma], methacrylic acid copolymer S [Eudragit S (trade name), Rohm Pharma] and the like; and a naturally-occurring material such as shellac.

A sustained release film coating base include, for example, a cellulose-based polymer such as ethylcellulose; and an acrylic acid-based polymer such as an aminoalkylmethacrylate copolymer RS [Eudragit RS (trade name), Rohm Pharma], an ethyl acrylate-methyl methacrylate copolymer suspension [Eudragit NE (trade name), Rohm Pharma] and the like.

Two or more of the coating bases described above may be used in admixture of appropriate proportion. A coating may be supplemented with an opacity-imparting agent such as titanium oxide and $Fe_3O_2$.

An injection formulation may be prepared by dissolving, suspending or emulsifying an active ingredient in an aqueous solvent (e.g. distilled water, physiological saline, Linger's solution) or in an oily solvent (e.g., vegetable oil such as olive oil, sesame oil, cottonseed oil and corn oil, propylene glycol) together with a dispersant (e.g. polysorbate 80, polyoxyethylene hardened castor oil 60), polyethylene glycol, carboxymethylcellulose, sodium alginate, preservative (e.g., methylparaben, propylparaben, benzylalcohol, chlrobutanol, phenol), osmotic agent (e.g., sodium chloride, glycerin, D-mannitol, D-sorbitol, glucose). In this case, if necessary, additives such as a solubilizing agent (e.g., sodium salicylate, sodium acetate), stabilizer (e.g., human serum albumin), pain-suppressing agent (e.g., benzyl alcohol) and the like may be added.

The daily dose of a hetercyclic compound having an angiotensin II antagonistic activity or a pharmaceutically acceptable salt thereof used in this invention is varied depending on the subject to be treated, the administration route, the disease to be treated and the condition, and for example in the case of oral administration, about 0.001 to 1000 mg, preferably about 0.1 to 50 mg active ingredient of the heterocyclic compound having an angiotensin II antagonistic activity or a pharmaceutically acceptable salt thereof is usually administered to a mammal, especially to an adult (50 kg body weight) at a single dose, which is administered preferably once to three times a day.

A TNF-α inhibitor of this invention can be used as a prophylactic and therapeutic agent for a disease involving the TNF-α to a mammal (for example, human, mouse, rat, rabbit, dog, cat, cattle, horse, pig, monkey). The disease involving a TNF-α is a disease which is developed or exacerbated as a result of the presence of the TNF-α, and can be treated through an inhibitory effect on the TNF-α. Such a disease include, for example, an inflammatory disease [e.g., diabetic complication such as retinopathy, nephropathy, neuropathy and major vascular disorders, diabetic nephropathy; arthritis such as chronic rheumatoid arthritis, osteoarthritis, rheumatoid myelitis and periosteosis; postoperative/posttraumatic inflammation; remedy of swelling; pharyngitis; cystitis; pneumonia; myocarditis; cardiomyopathy; atopic dermatitis; inflammatory intestinal disease such as Crohn's disease and ulcerative colitis; meningitis; inflammatory ophthalmic disease; inflammatory pulmonary disease such as pneumonia, silicotuberculosis, pulmonary sarcoidosis and pulmonary tuberculosis], circulatory disease (e.g., chronic heart failure including arrhythmia, angina pectris, myocardial infarction, cardiac insufficiency and congestive heart failure, arteriosclerosis including atherosclerosis, hypertension, deep vein thrombosis, occlusive peripheral circulation failure, ischemic cerebral circulation failure, disseminated intravascular coagulation syndrome, Raynaud's disease, Buerger disease), portal hypertension, pulmonary hypertension, allegic disease such as asthma, allergic rhinitis, conjunctivitis, digestive tract allergy, pollinosis and anaphylaxis, chronic occlusive pulmonary disease, collagenosis (e.g., lupus erythematosus, pachyderma, polyarteritis), Crohn's disease, autoimmune hemolytic anemia, psoriasis, hepatic disease such as hepatitis including chronic disease and cirrhosis, pancreatic disease such as pancreatitis, neurodegenerative disease (e.g., Alzheimer's disease, Parkinson's disease, amyotrophic lateral sclerosis, AIDS encephalopathy), central nerve failure (e.g., cerebrovascular failure such as cerebral hemorrhage and cerebral infarction and its sequela, cranial trauma, spinal damage, cerebral edema, dementia, memory failure, consciousness failure, multiple sclerosis), toxemia (e.g., sepsis, septic shock, endotoxic shock, gram negative sepsis, toxin shock syndrome), climacteric failure, gestosis, adiposis, hyperlipidemia, hypercholesteremia, abnormal glucose tolerance, solid tumor, tumor (e.g., malignant melanoma, malignant lymphoma, cancer of digestive organ (e.g., stomach, intestine)), cancer and accompanying cachexia, endocrine disease (Addison disease, Cushing's syndrome, melanocytoma, primary aldosteronism), Creutzfeldt-Jakob disease, viral infection (e.g., infections with cytomegalovirus, influenzae virus, herpes virus and the like), post-percutaneous coronary arterioplasty vascular hypertrophy or occlusion, post-PTCA/stenting/bypass surgery vascular reocclusion/restenosis, post-intervention vascular hypertrophy or occlusion, suppression of implantatin-induced vascular failure and rejection, dialytic hypotension, glaucoma, high ocular tension, myasthenia gravis, chronic defatigation, bone disease (e.g. fracture, re-fracture, osteoporosis, osteomalacia, bone Behet disease, ankylosing spondylitis, chronic rheumatoid arthritis, osteogonarthritis as well as articular tissue destruction in disease related thereto).

A TNF-α-inhibitor of the present invention may be used alone in a therapy or may be used in combination with other pharmaceutically active component including hypolipidemic agent or hypocholesteric agent, HMG-Co A reductase (3-hydroxy-3-methylglutaryl coenzyme A reductase) inhibitor, myocardial protecting agent, coronary artery disease-treating agent, other hypertention-treating agent, chronic heart failure-treating agent, diabetes-treating agent, other insulin sensitivity-modifying agent, hypothyroidism-treating agent, nephrosis syndrome-treating agent, anti-inflammatory agent (NSAIDS and the like), bone disease-treating agent (osteoporosis-treating agent and the like) or chronic renal failure-treating agent, and in such a case any of these components is administered preferably as an oral formulation, or as a rectal formulation in the form of a suppository if necessary. A possible component to be combined as described above include, for example, a fibrate [e.g., clofibrate, benzafibrate, GEMFIBRODIL], nicotinic acid, its derivatives and analogues [e.g., ACIPIMOX and probucol], bile acid-binding resin [e.g., cholestyramine, colestipol], cholestrol absorption inhibitor [e.g., sitosterol, neomycin], squalene epoxidase inhibitor [e.g., NB-598 and analogues] and the like.

Other components which can be combined are oxidesqualene-lanosterol cyclase, for example, decalin derivatives, azadecalin derivatives and indan derivatives.

Hypertension-treating agents: diuretics [e.g., furosemide (Lasix), bumetamide (Lunetoron), azosemide (Diart)], hypotensive agents [e.g., ACE inhibitor (enalapril maleate (Renivace)) and Ca antagonist (manidipine, amlodipine), α or β recepter blockers].

Chronic heart failure-treating agents: cardiacs [e.g., cardiotonic glucoside (digoxin and the like), β receptor stimulant (chatecholamine formulation such as denopamine and dobutamine) and PDE inhibitor], diuretics [e.g. furosemide (Lasix), spironolactone (Aldactone)], ACE inhibitors [e.g., enalapril maleate (Renivace)], Ca antagonist [e.g., amlodipine] and β receptor blocker.

Anti-arrhythmic agent: Disopyramide, lidocaine, quinidine sulfate, flecainide acetate, mexiletine hydrochloride, amiodarone hydrochloride and β blocker, Ca antagonist and the like.

Diabetes-treating agents: Actos, Rosiglidazone, Kinedak, BENFIL, Humulin, Euglucon, Glimicron, Daonil, Nobolin, Monotard, insulins, Glucobay, Dimelin, Rastinon, BASILCON, Deamelin S, Iszilin;

Hypothyroidism-treating agents: Dried thyroid (Thyreoid), sodium levothyroxine (Thyradin S), liothyronidine sodium (Thyronin, Thyronamin);

Nephrosis syndrome-treating agents: Usually, a first choice steroid therapy employs prednisolon (Predonine), sodium prednisolon succinate (Predonine), sodium methylprednisolon succinate (Solu-medrol), betamethasone (Rinderon) and the like. An anti-coagulation therapy employs antiplatelets and anti-coagulants such as dipyridamole (BELSANTIN), dilazep hydrochloride (Comelian), tyropidine, clopidogrel, FXa inhibitor;

HMG-Co A reductase inhibitors: cerivastatin, atrovastatin, pravastatin, simvastatin, itavastatin, lovastatin, fluvastatin, (+)-3R,5S-7-[4-(4-fluorophenyl)-6-isopropyl-2-(N-methyl-N-methanesulfonylamino)pyrimidin-5-yl]-3,5-hydroxy-6 (E)-heptenoic acid and the like;

Bone disease-treating agents: calcium formulations (e.g., calcium carbonate), calcitonin formulations, active vitamin $D_3$ formulations (e.g., alfacalcidol, (Alfarol and the like), calcitriol (Rocaltrol)), sex hormones (e.g., estrogen, estranediol), hormone formulations [e.g., conjugated estrogen (Premarin)], IPRIFLAVON formulations (Osten and the like), vitamin $K_2$, vitamin $K_2$ formulations [e.g., menatetrenone (Glakay) and the like], bisphosphonic acid-based formulations (etidronate and the like), prostaglandin A1, fluorine compounds (e.g., sodium fluoride), osteogenetic protein (BMP), fibroblast growth factor (FGF), platelet-derived growth factor (PDGF), transforming growth factor (TGF-β), insulin-like growth factor-1 and 2 (IGF-1, -2), parathyroidal hormone (PTH), compounds described in EP-A1-376197, EP-A1-460488 and EP-A1-719782 (e.g., (2R, 4S)-(-)-N-[4-(diethoxyphosphorylmethyl)phenyl]-1,2,4,5-tetrahydro-4-methyl-7,8-methylenedioxy-5-oxo-3-benzothiepin-2-carboxamide) and the like;

Chronic renal failure-treating agents: diuretics [e.g., furosemide (Lasix), bumetamide (Lunetoron), azosemide (Diart)], hypotensive agents [e.g., ACE inhibitor (enalapril maleate (Renivace)) and Ca antagonist (manidipine), α receptor blocker and the like;

are combined and administered preferably through an oral route.

Further, the TNF-α inhibitor of the present invention is useful for preventing and treating a thrombosis. In that case, it may be given alone or in combination with known pharmaceuticals listed below, preferably through an oral route.

Thrombosis-preventing and treating agents: Anti-coagulants [e.g., heparin sodium, heparin calcium, warfarin calcium (Warfarin), coagulant factor Xa inhibitor and coagulation-fibrogenlytic balance-modifying agent], thrombolytic agents [e.g., tPA, urokinase], antiplatelet agents [e.g., aspirin, sulfinpyrazone (ANTULAN), dipyridamole (Persantin), ticlopidine (Panaldine), cilostazole (Pletal), GPIIb/IIIa antagonist (ReoPro)] and the like.

Coronary dilators: Nifedipine, diltiazem, NICORADIL, nitrite formulations and the like.

Myocardial protectants: heart ATP-K opening agent, Na—H exchange inhibitor, endothelin antagonist, urotensin antagonist and the like.

Anti-inflammatory agents: Aspirin, acetaminophen, non-steroidal anti-inflammatory agents [e.g., indomethasin], steroids [e.g., dexamethasone] and the like.

Anti-allegic agents: Anti-histamine agents [e.g., chlorphenylamine maleate], stimulative therapy agents [e.g., bucillamine], as well as azelastin, seratrodast, tranilast, oxatomide, Stronger Neo-Minophagen C, tranexamic acid, ketotifen fumarate and the like.

Anti-tumor agents: Alkylating agents, metabolic antagonists, anti-tumor antibiotic formulations, anti-tumor plant component formulation and other anti-tumor agents.

Central nervous system agents: Anti-anxiety agent, hypnotic sedatives, anesthetics, spasmolytic agents, autonomice agents, anti-parkinsonism agents and other psychoneurotic agents.

Furthermore, anti-obesity agents, anti-rheumatic agents and the like.

In addition, a therapy using various biological factors or respective gene transduction (e.g., ischemic disease therapy using angiogenesis promoting factors such as HGF and VEGF or respective gene transduciton) and the like.

A TNF-α inhibitor of the present invention can be used in combination with any of those listed above simultaneously or at a certain time interval.

When any of those pharmaceuticals is used in combination, each may be mixed separately or simultaneously with pharmacologically acceptable carrier, excipient, binder, diluent and the like to prepare into a formulation, which can be administered as a pharmaceutical composition orally or parenterally. When the active ingredients are formulated separately, the resultant individual formulations may be mixed just before use for example using a diluent, while the individual formulations may be given simultaneously or at a certain time interval to an identical subject. A kit product for administration with mixing individual formulations just before use using diluent (for example, a injection kit containing ampoules containing individual powder agents and a diluent for mixing and dissolving two or more agents just before use) and a kit product for administering separately prepared individual formulations simultaneously or separately at a certain time interval to an identical subject (for example, a kit of tablets for administering two or more tablets simultaneously or separately at a certain time interval in which the tablets containing individual agents are placed in an identical or separate bags provided if necessary with the label indicating the timing of the administration) are also encompassed in a pharmaceutical according to the present invention.

A heterocyclic compound having a angiotensin II antagonistic activity used in the present invention can be used orally or parenterally, through injection, drip infusion, inhalation, rectal administration or topical administration, and can be used as it is or as a formulation of a pharmaceutical composition (for example, powder, granule, tablet, pill, capsule, injection, syrup, emulsion, elixir, suspension, solution). That is, a heterocyclic compound having an angiotensin II antagonistic activity according to the present invention can be used alone or in a mixture with a pharmaceutically acceptable carrier (adjuvant, excipient, auxiliary agent and/or diluent).

A pharmaceutical composition can be formulated by a known method. Such a formulation can be produced usually by mixing/kneading an active ingredient with additives such as an excipient, diluent, carrier and the like. The term "parenteral" administration employed here means to include a subcutaneous injection, intravenous injection, intramuscular injection, intraperitoneal injection and drip infusion. A formulation for injection, such as a suspension in an aseptic water for injection or an oily suspension, can be prepared by a method known in the art using a suitable dispersant or wetting agent and suspending agent. The aseptic injection formulation may be an injectable aseptic solution or suspension in a diluent or solvent which is non-toxic and can be given parenterally, such as an aqueous solution. Vehicles and solvents which can be employed are water, Linger's solution, isotonic saline and the like. In addition, an aseptic non-volatile oil can usually be employed as a solvent or suspending medium. For this purpose, any non-volatile oil or fatty acid may be employed, including naturally occurring or synthetic or semi-synthetic fatty oils or fatty acids as well as naturally occurring or synthetic or semi-synthetic mono-, di- and triglycerides.

A suppository for rectal administration can be produced by mixing an active ingredient with a suitable non-irritative auxiliary agent which is solid at ambient temperature but liquid at a temperature in an intestine and melts in rectum whereby releasing the active ingredient, such as cocoa butter and polyethylene glycols.

A solid dosage form for oral administration may for example be a powder, granule, tablet, pill, capsule and the like, as mentioned above. A formulation of such dosage form can be produced by mixing and/or kneading an active ingredient with at least one additive such as sucrose, lactose, cellulose sugar, mannitol (D-mannitol), maltitol, dextran, starches (e.g., corn starch), microcrystalline cellulose, agar, alginates, chitins, chitosans, pectins, tragacanth gums, gum arabic, gelatins, collagens, casein, albumin, synthetic or semi-synthetic polymers or glycerides. Such a dosage form may contain, as usual, further additives such as an inert diluent, lubricant such as magnesium stearate, preservative such as parabens and sorbic acid, antioxidant such as ascorbic acid, α-tocopherol and cysteine, disintegrant (e.g., sodium croscarmellose), binder (e.g., hydroxypropyl cellulose), thickening agent, buffering agent, sweetener, flavor, perfume and the like. A tablet or pill may further be enteric-coated. A liquid formulation for oral use includes a pharmaceutically acceptable emulsion, syrup, elixir, suspension and solution, which may contain an inert diluent used ordinarily in the art such as water and may also contain additives, if necessary. Such a liquid formulation for oral use can be produced by a customary method, for example by mixing an active compound with an inert diluent and other additives if necessary. An oral formulation contain generally 0.01 to 99% by weight, preferably 0.1 to 90% by weight, usually 0.5 to 50% by weight of an active compound of the present invention, although the amount may vary depending on the dosage forms.

The dose in a certain patient is decided depending on the age, body weight, general condition, sex, diet, administration time, administration mode, excretion rate, combination of medicaments, severity of the condition being treated, as well as other factors.

While the daily dose of a TNF-α inhibitor comprising a heterocyclic compound having an angiotensin II antagonistic activity used in this invention or its salt may vary depending on the condition and the body weight of the patient, type of the compound employed, administration route and the like, it can be administered as a prophylactic/therapeutic agent for an inflammatory disease in adults (about 60 kg body weight) at an oral daily dose of about 0.01 to 1000 mg, preferably at about 0.1 to 50 mg as an active ingredient, and at a parenteral daily dose of about 0.001 to 100 mg, preferably at about 0.01 to 50 mg, usually about 0.1 to 20 mg as an active ingredient.

BEST MODE FOR CARRYING OUT THE INVENTION

Hereinafter, the present invention is further detailed by the following Examples, which are not intended to restrict the present invention.

EXAMPLES

A TNF-α inhibitor comprising a heterocyclic compound having an angiotensin II antagonistic activity in this invention or its salt can be produced for example by the following prescriptions.

Example 1

Capsules

| | | |
|---|---|---|
| (1) | Candesartan cilexetil | 30 mg |
| (2) | Lactose | 90 mg |
| (3) | Microcrystalline cellulose | 70 mg |
| (4) | Magnesium stearate | 10 mg |
| | 1 Capsule | 200 mg |

After mixing Components (1), (2), (3) and a half of Component (4), the mixture is granulated. Then the remainder of Component (4) is added and the entire is filled in gelatin capsules.

Example 2

Tablets

| | | |
|---|---|---|
| (1) | Candesartan cilexetil | 30 mg |
| (2) | Lactose | 35 mg |
| (3) | Corn starch | 150 mg |
| (4) | Microcrystalline cellulose | 30 mg |
| (5) | Magnesium stearate | 5 mg |
| | 1 Tablet | 250 mg |

After mixing Components (1), (2), (3), ⅔ of Component (4) and ½ of Component (5), the mixture is granulated. To the resultant granule, the remainder of Components (4) and (5) are added and compressed into tablets.

Experimental Example 1

TNF-α Inhibiting Effect

According to the method described in K. Murase et al., Diabetologia 41: 257–264, 1998, a test drug is administered to model animals having obesity and diabetic condition, and by determining the change in the levels of a TNF-α in blood or tissues, the TNF-α inhibiting effect of the compound of this invention is confirmed.

Industrial Applicability

A TNF-α inhibitor of the present invention has an excellent TNF-α inhibiting effect and is useful as preventives/remedies for inflammatory diseases.

What is claimed is:

1. A method for inhibiting a TNF-α in mammals comprising administering to a mammal an effective amount of a heterocyclic compound having an angiotensin II antagonistic activity which is represented by the formula:

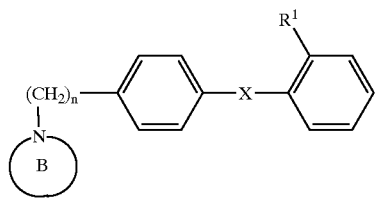

wherein ring B is an optionally substituted nitrogen-containing heterocyclic ring, $R^1$ is a group capable of forming an anion or a group capable of being converted into such a group, X denotes that a phenylene group and a phenyl group are bound directly or through a spacer having 2 or less of atomic chains, and n is an integer of 1 or 2, or its prodrug or a salt thereof, provided that the compound is not (5,7-dimethyl-1-{[2'-(1H-tetrazol-5-yl)-1,1'-biphenyl-4-yl]methyl}-3,4-dihydro-1,6-naphthylidine-2(1H)-one).

2. The method according to claim 1, wherein the heterocyclic compound is a compound having an oxygen atom in its molecule.

3. The method according to claim 1, wherein the heterocyclic compound is a compound having an ether bond or a carbonyl group.

4. The method according to claim 1, wherein ring B is an optionally substituted 5-membered nitrogen-containing aromatic heterocyclic ring.

5. The method according to claim 1, wherein ring B is an optionally substituted 5-membered nitrogen-containing heterocyclic ring.

6. The method according to claim 1, wherein ring B is an optionally substituted imidazole ring.

7. The method according to claim 1, wherein the heterocyclic compound is a compound represented by the formula (I):

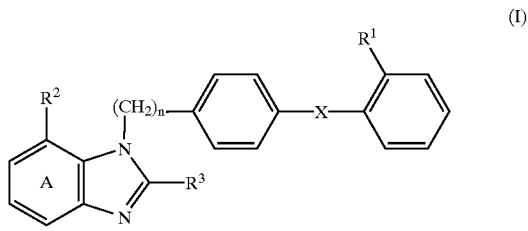

wherein $R^1$ is a group capable of forming an anion or a group capable of being converted into such a group, X denotes that a phenylene group and a phenyl group are bound directly or through a spacer having 2 or less of atomic chains, n is an integer of 1 or 2, ring A is a further optionally substituted benzene ring, $R^2$ is a group capable of forming an anion or a group capable of being converted into such a group, $R^3$ is an optionally substituted hydrocarbon residue which may be bound through a heteroatom.

8. The method according to claim 1, wherein the heterocyclic compound is losartan, eprosartan, candesartan cilexetil, candesartan, telmisartan, irbesartan, olmesartan or tasosartan.

9. The method according to claim 1, wherein the heterocyclic compound is 2-ethoxy-1-[[2'-(1H-tetrazol-5-yl)biphenyl-4-yl]methyl]benzimidazole-7-carboxylic acid.

10. The method according to claim 1, wherein the heterocyclic compound is 1-(cyclohexyloxycarbonyloxy)ethyl 2-ethoxy-1-[[2'-(1H-tetrazol-5-yl)biphenyl-4-yl]methyl]benzimidazole-7-carboxylate.

11. The method according to claim 1, wherein the heterocyclic compound is 2-ethoxy-1-[[2'-(2,5-dihydro-5-oxo-1,2,4-oxadiazol-3-yl)biphenyl-4-yl]methyl]benzimidazole-7-carboxylic acid.

* * * * *